United States Patent
Rice

(10) Patent No.: US 6,600,946 B1
(45) Date of Patent: Jul. 29, 2003

(54) METHODS AND APPARATUS FOR QUANTIFYING DERMAL HYDRATION

(75) Inventor: Robert R. Rice, Simi Valley, CA (US)

(73) Assignee: The Boeing Company, Seattle, WA (US)

(*) Notice: Subject to any disclaimer, the term of this patent is extended or adjusted under 35 U.S.C. 154(b) by 286 days.

(21) Appl. No.: 09/637,961

(22) Filed: Aug. 11, 2000

(51) Int. Cl.⁷ .................................................. A61B 6/00
(52) U.S. Cl. ........................ 600/473; 600/340; 600/407; 600/476; 250/339.1; 250/341.8
(58) Field of Search ................................. 600/340, 600, 600/318, 322, 323, 407, 473, 476, 304, 310, 306; 128/920, 923, 924, 848, 847

(56) References Cited

U.S. PATENT DOCUMENTS

| | | | |
|---|---|---|---|
| 5,348,002 A | * | 9/1994 | Caro ............................ 356/39 |
| 5,348,003 A | * | 9/1994 | Caro ............................ 356/39 |
| 5,353,790 A | * | 10/1994 | Jacques et al. .............. 250/574 |
| 5,529,065 A | * | 6/1996 | Tsuchiya .................... 600/310 |
| 5,776,060 A | | 7/1998 | Smith et al. |
| 5,847,816 A | | 12/1998 | Zediker et al. |
| 5,867,257 A | | 2/1999 | Rice et al. |
| 5,983,120 A | * | 11/1999 | Groner et al. .............. 356/364 |
| 6,353,226 B1 | * | 3/2002 | Khalil et al. ............. 250/341.8 |

* cited by examiner

Primary Examiner—Marvin M. Lateef
Assistant Examiner—Jeoyuh Lin
(74) Attorney, Agent, or Firm—Alston & Bird LLP

(57) ABSTRACT

Dermal hydration is determined in a target region of a human subject by determining a relationship between first and second measurements. The first measurement is a measurement of a first type of electromagnetic radiation that has been reflected from the target region, the second measurement is a measurement of a second type of electromagnetic radiation that has been reflected from the target region, and the second type of electromagnetic radiation is absorbed by liquid, namely water or perspiration, to a greater degree than the first type of electromagnetic radiation is absorbed by the liquid. The electromagnetic radiation that is reflected from the region and measured is initially transmitted to the region from a remote location, and the transmitted electromagnetic radiation is not visible to a naked human eye. An examination being carried out in accordance with the present invention can be carried out while the region is moving, by tracking the region. As a result, examinations carried out in accordance with the present invention can advantageously be relatively noninvasive, and the subject being examined need not even be aware of the examination.

30 Claims, 3 Drawing Sheets

METHODS AND APPARATUS FOR QUANTIFYING DERMAL HYDRATION

FIELD OF THE INVENTION

The present invention relates generally to monitoring physiological characteristics and, more particularly, to measuring dermal hydration.

BACKGROUND OF THE INVENTION

It can be useful in a variety of situations to monitor physiological characteristics. For example, an instrument for detecting and measuring physiological changes that accompany emotional stress is commonly referred to as a polygraph. A polygraph typically includes multiple sensors that are directly connected to an individual's body for measuring multiple physiological parameters. Standard polygraph sensors include a blood pressure cuff, a pair of respiration belts, and skin resistance finger electrodes, all of which are coupled to data collection and recordation equipment.

The skin resistance finger electrodes of a polygraph are used to measure galvanic skin response (GSR). GSR reflects the emotional stress level of the individual being tested by providing a measure of skin conductivity or resistance, which is largely influenced by sweat gland activity. The sweat glands secrete perspiration that flows to the surface of the skin. The perspiration includes liquid and electrolytes; therefore, perspiration facilitates electrolytic conduction at the surface of the skin. GSR testing typically includes attaching electrodes to separate fingers of the same hand and attaching a galvanometer to the electrodes to measure the conductance or resistance between the electrodes.

Having to attach electrodes to an individual to measure their GSR can be disadvantageous is some circumstances. The electrodes are invasive, and therefore they can be uncomfortable to the individual being examined and can themselves cause the individual being tested to become stressed. The invasive and stressful nature of conventional GSR testing can disadvantageously contribute to people's hesitance to being subjected to GSR and polygraph examinations, and to some degree also complicates the interpretation of the results of such examinations.

Another technique for monitoring physiological characteristics is disclosed in U.S. Pat. No. 5,867,257 to Rice et al., which is incorporated herein by reference. The Rice et al. patent discloses a battlefield personnel threat detection system for identifying and analyzing vibrations, such as vibrations caused by the heartbeat of an animal. More specifically, a micro-doppler ladar beam is transmitted, scattered back, collected and analyzed. Whereas such use of a micro-doppler ladar provides for noninvasive monitoring of physiological characteristics, it does not lend itself to GSR-like measurements.

Accordingly, there is a need in the art for methods and apparatus that are capable of at least generally noninvasively monitoring a physiological characteristic and that can at least potentially serve as surrogates for GSR testing.

SUMMARY OF THE INVENTION

The present invention solves the above and other problems by providing methods and apparatus that utilize electromagnetic radiation in the furtherance of determining dermal hydration. In accordance with one aspect of the present invention, measurements of dermal hydration can serve as surrogates for GSR measurements.

In accordance with one aspect of the present invention, dermal hydration is determined in a target region of a human subject by determining a relationship between first and second measurements. The first and second measurements are measurements of electromagnetic radiation that has been reflected from the target region. In accordance with one embodiment, the first measurement is a measurement of a first type of electromagnetic radiation that has been reflected from the target region, and the second measurement is a measurement of a second type of electromagnetic radiation that has been reflected from the target region. To detect and measure dermal hydration, the second type of electromagnetic radiation is absorbed by liquid, namely water or more specifically perspiration, to a greater degree than the first type of electromagnetic radiation is absorbed by the liquid.

In accordance with one aspect of the present invention, the electromagnetic radiation that is reflected from the target region and measured is initially transmitted to the target region from a remote location, and the transmitted electromagnetic radiation, such as a laser beam, is not visible to a naked human eye. In accordance with one aspect of the present invention, dermal hydration of a target region is determined while the target region is moving, by tracking the target region. As a result, examinations carried out in accordance with the present invention can advantageously be generally noninvasive and remotely administered, and the subject being examined need not even be aware of the examination.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

In accordance with a first embodiment of the present invention, methods and apparatus are provided for quantifying dermal hydration at a target region of a human subject. The dermal hydration is quantified through the use of electromagnetic radiation. In accordance with the first embodiment, the target region is the exterior surface of a portion of the subject's skin, and measurements of dermal hydration provide an indication of the amount of liquid, namely water and most specifically perspiration, closely associated with the surface of the skin in the target region. As noted above, perspiration includes liquid water and electrolytes, and therefore perspiration facilitates electrolytic conduction at the surface of the skin. As also noted above, GSR testing typically includes attaching electrodes to a subject's hand and attaching a galvanometer to the electrodes to measure the conductance or resistance of the subject's skin. In accordance with one aspect of the present invention, the methods and apparatus of the present invention can serve as surrogates for GSR testing, meaning that the measured instantaneous levels of dermal hydration at the surface of the subject's skin can be at least generally correlated with stress in a manner at least generally similar to the correlations made with GSR data. In addition, the methods and apparatus of the present invention can provide advantages that are generally not available with GSR testing. For example and in accordance with the first embodiment, dermal hydration is quantified through the use of electromagnetic radiation that is not perceptible by the human subject (i.e., not detectable by a naked eye of a human), so that the present invention can be used in generally noninvasive and covert examinations. As a result and advantageously, examinations carried out in accordance with one aspect of the present invention do not themselves impact the emotional stress level of the individuals being examined, because the individuals being examined are not aware of the examinations.

Figure 1:
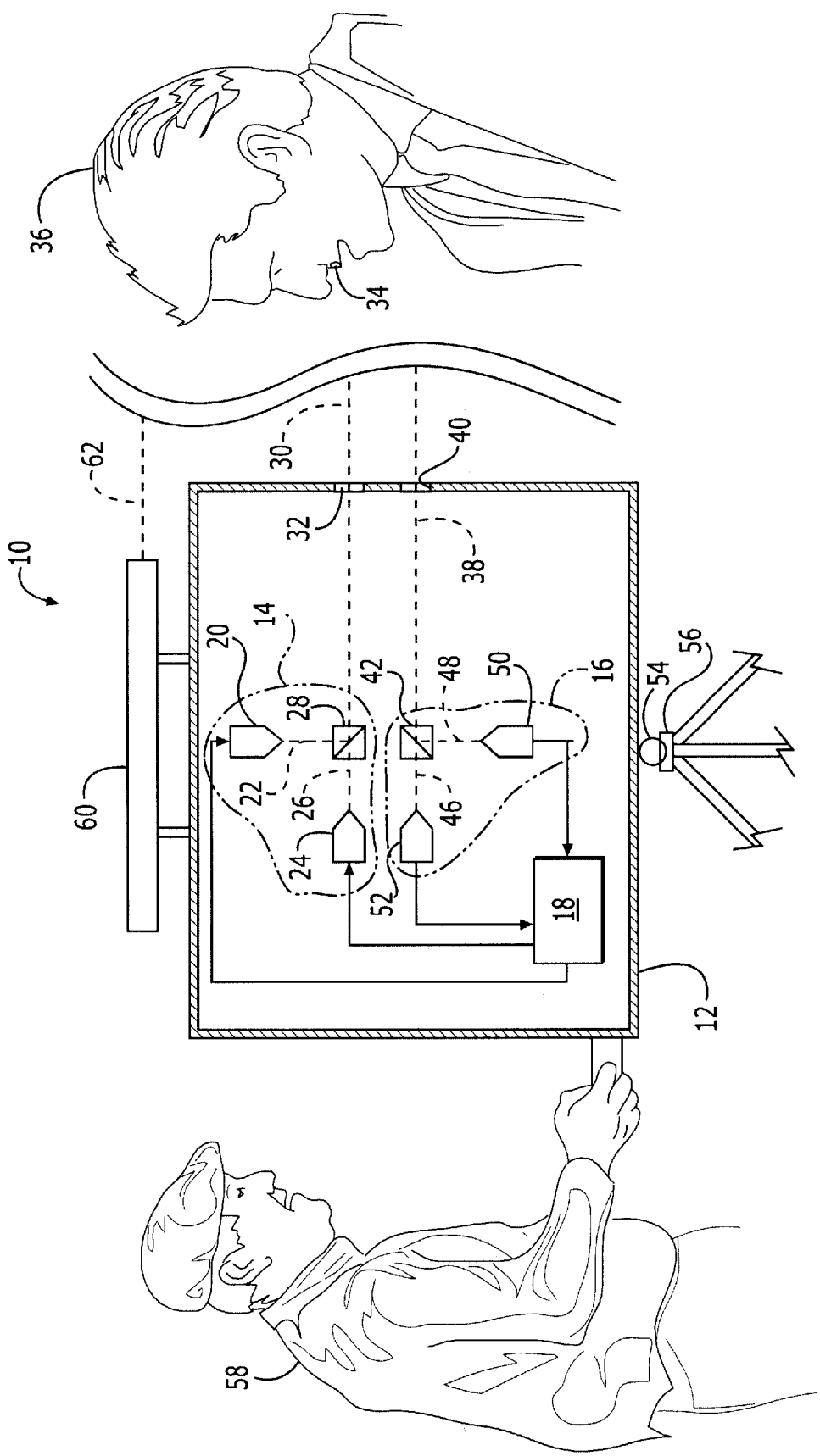
FIG. 1 is a partially cross-sectioned, diagrammatic and environmental view illustrating an apparatus for determining dermal hydration, in accordance with a first embodiment of the present invention.

Referring to FIG. 1, an instrument for quantifying dermal hydration is indicated generally at 10, in accordance with the first embodiment of the present invention. Numerous variations to that which is illustrated in and described with reference to FIG. 1 are within the scope of the present invention.

In accordance with the first embodiment, the instrument 10 includes a housing 12 containing a transmitting mechanism 14, a detecting mechanism 16 and a controller/processor 18 operationally associated with the transmitting and detecting mechanisms. In accordance with the first embodiment, the controller/processor 18 is preferably a computerized device having one or more computer processors, software modules, computer-readable storage mediums, and input and output hardware cooperative for carrying out operations of the present invention. For illustrative purposes in FIG. 1, the components that make up the transmitting and detecting mechanisms 14, 16 are respectively circled by lines made up repeating series of two short dashes alternating with one long dash, and those components are discussed in greater detail below.

The transmitting mechanism 14 includes a high wavelength transmitter 20 for transmitting electromagnetic radiation in the form of a high wavelength signal 22. Similarly, the transmitting mechanism 14 further includes a low wavelength transmitter 24 for transmitting electromagnetic radiation in the form a low wavelength signal 26. In this Detailed Description of the Invention section of this disclosure, the use of the terms "high wavelength" and "low wavelength" are relative terms only in the sense that high wavelength means higher than low wavelength, and vice versa. The transmitting mechanism 14 further includes a transmitting beam combiner 28 that is positioned in the path of both the high and low wavelength signals 22, 26. The transmitting beam combiner 28 is operative for combining the high and low wavelength signals 22, 26 into a transmitted beam 30 that passes through a transmit aperture 32. The transmit aperture 32 is defined by a structural portion of the instrument 10, such as through a portion of the housing 12 or any other suitable component of the instrument. In accordance with the first embodiment, an acceptable example of the transmitting beam combiner 28 is a dichroic beam splitter, or the like.

As will be discussed in greater detail below, in accordance with the first embodiment, the instrument 10 is operated so that the transmitted beam 30 is incident upon a target region 34 of a human subject 36. In accordance with the first embodiment, the target region 34 is a predetermined portion of the surface of the skin of the human subject 36. The predetermined portion is preferably commonly exposed and is also commonly wetted with perspiration while the human subject 36 being examined is under stress. That is, the target region 34 can be the forehead, the region just above the upper lip, the neck, or the like. Accordingly, the present invention is not limited to the specific target region 34 identified in FIG. 1.

As a result of the transmitted beam 30 being incident upon the target region 34, at least some of the transmitted beam is reflected back toward the instrument 10, and that reflected portion is characterized herein as reflected electromagnetic radiation 38. At least some of the reflected electromagnetic radiation 38 passes through a receive aperture 40 defined through a structural portion of the instrument 10, such as through a portion of the housing 12 or any other suitable component of the instrument. The reflected electromagnetic radiation 38 that passes through the receive aperture 40 is incident upon the detecting mechanism 16. Accordingly, the detecting mechanism 16 has a field of view. In accordance with the first embodiment, the instrument 10 is constructed so that the field of view of the detecting mechanism 16 is upon the target region 34 at the same time the transmitted beam 30 is upon the target region. Therefore, the reference number 34 can be characterized as referring to the transmitted beam 30, the field of view, and the target region while the transmitted beam is incident upon the target region.

In accordance with the first embodiment, the detecting mechanism 16 includes a detecting beam splitter 42 that splits the reflected electromagnetic radiation 38 into a passed beam portion 46 and a reflected beam portion 48. In accordance with the first embodiment, an acceptable example of the detecting beam splitter 42 is a dichroic beam splitter, or the like. In accordance with the illustrated version of the first embodiment, the detecting mechanism 16 further includes a high wavelength detector 50 that the reflected beam portion 48 is incident upon, and a low wavelength detector 52 that the passed beam portion 46 is incident upon.

Although the instrument 10 of the first embodiment is described as having separate apertures 32 and 40 for the transmitted beam 30 and the reflected electromagnetic radiation 38, respectively, it is within the scope of the present invention for both the transmitted beam and the reflected electromagnetic radiation to pass through the same aperture. Notwithstanding the foregoing, the use of separate apertures 32, 40 is preferred to minimize the detrimental effects of back-scatter.

In accordance with the first embodiment, the high and low wavelength transmitters 20, 24 are selected so that the high wavelength signal 22 is absorbed by liquid, namely water and most preferably perspiration, to a greater degree than the low wavelength signal 26. Whereas the first embodiment of the present invention is described in the context of the high wavelength signal 22 being absorbed by liquid to a greater degree than the low wavelength signal 26, it is possible that the present invention can be carried out through the use of a low wavelength signal that is absorbed by liquid to a greater degree than a high wavelength signal, and hence the scope of the present invention is not intended to be limited to particular wavelengths or relationships therebetween. That is, it is within the scope of the present invention to utilize a variety of different wavelengths, so long as the wavelengths being used preferably have measurable differences in the degree to which they are absorbed by liquid, namely water and most preferably perspiration. That is, the selected wavelengths preferably have widely different absorption coefficients in liquid, namely water and most preferably perspiration. Further, more than two wavelength bands may be used simultaneously if beneficial.

In contrast and in accordance with an alternative embodiment of the present invention, the transmitted beam 30 may have generally only a single wavelength, and measurements of the resulting reflected beam portion 38 may be trended over time by comparing sequential measurements thereof to quantify the amount of liquid, namely water and most preferably perspiration, in the target region 34. Whereas it is possible to utilize a single wavelength, it is advantageous to use multiple wavelengths with different absorption coefficients, with one of the wavelengths serving as a baseline. This allows for variations in the intensity of the reflected electromagnetic radiation 38 that are not attributed to variations in dermal hydration to be advantageously excluded from the pertinent analysis, as will become apparent in the following.

For the sake of completeness rather than for limiting the scope of the present invention, examples of acceptable high and low wavelength signals 22, 26 and the transmitting and detecting mechanisms 14, 16 are described below, in accordance with the first embodiment. The high wavelength transmitter 20 is acceptably an infrared laser diode or a light emitting diode operative for transmitting the high wavelength signal 22 so that it includes at least one wavelength selected from the range of approximately 1500–1600 nm. Even more specifically, the high wavelength transmitter 20 preferably is operative so that the wavelength of the high wavelength signal 22 is in the range of approximately 1500–1600 nm. Similarly, the low wavelength transmitter 24 is acceptably an infrared laser diode or light emitting diode operative for transmitting the low wavelength signal 26 so that it includes at least one wavelength selected from the range of approximately 1000–1100 nm. Even more specifically, the low wavelength transmitter 24 is operative so that the wavelength of the low wavelength signal 26 is in the range of approximately 1000–1100 nm.

The high wavelength detector 50 is acceptably a photodiode operative for providing an electrical signal that varies at least somewhat proportionally in response to the intensity of electromagnetic radiation incident thereon and having wavelengths in the range of approximately 1500–1600 nm. Similarly, the low wavelength detector 52 is acceptably a photodiode operative for providing an electrical signal that varies at least somewhat proportionally in response to the intensity of electromagnetic radiation incident thereon and having wavelengths the range of approximately 1000–1100 nm. Accordingly, the signals provided by the high and low wavelength detectors 50, 52 can be generally characterized as providing measurements of the electromagnetic radiation to which the high and low wavelength detectors are respectively responsive.

In accordance with the first embodiment, the housing 12 of the instrument 10 is mounted to a pivot 54 that is carried by a tripod 56, or the like, so that the orientation of the housing can be readily adjusted by an operator 58. Also in accordance with the first embodiment, a conventional sight 60 is mounted to the housing 12. As illustrated in FIG. 1, the conventional sight 60 is telescopic and defines a line of sight 62, and preferably the telescope sight has internal cross hairs (not shown), or the like, to facilitate aiming. In accordance with the first embodiment, the instrument 10 is constructed so that while the transmitted beam 30 is upon the target region 34 and the operator 58 is looking through the telescopic sight 60, the line of sight 62 is upon the target region and the cross hairs of the sight are centered upon the target region. In accordance with the first embodiment and as will be discussed in greater detail below, for initial targeting and tracking purposes, the operator 58 pivots the instrument 10 relative to the tripod 56 and utilizes the telescopic sight 60 so that the transmitted beam 30 is aimed at the target region 34, and at the same time the field of view of the detecting mechanism 16 is positioned over the target region due to the alignment of the transmitted beam and the field view. Alternatively, the instrument 10 may be similarly used while being carried on the shoulder of the operator 58 or while being supported in any other manner. In accordance with a second embodiment of the present invention that is discussed in greater detail below, rather than relying upon actions of the operator 58 to manually track the target region 34, the instrument 10 is equipped with an automated tracking system for tracking the target region.

In accordance with the first embodiment of the present invention and generally described, the instrument 10 is utilized to carry out methods of quantifying the amount of liquid, namely water and most preferably perspiration, in the target region 34 by making differential reflectivity measurements at multiple wavelengths. The instrument 10 is just one example of a system that can be utilized to carry out the methods of the present invention.

Figure 2:
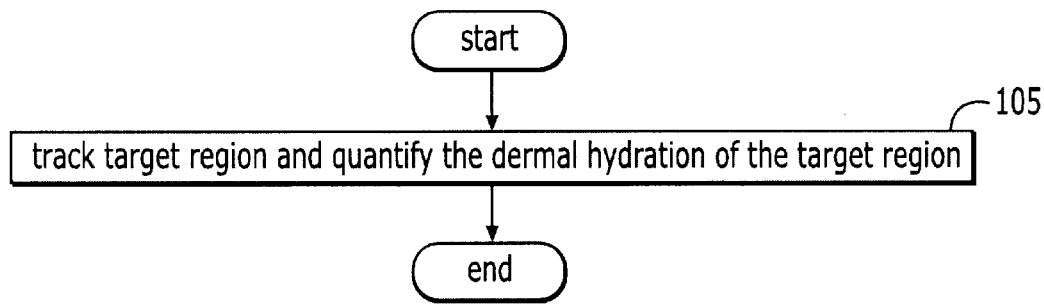
FIG. 2 presents a flow chart illustrating high level operations performed to remotely quantify dermal hydration at a target region of a moving human subject, in accordance with the first embodiment.
Figure 3:
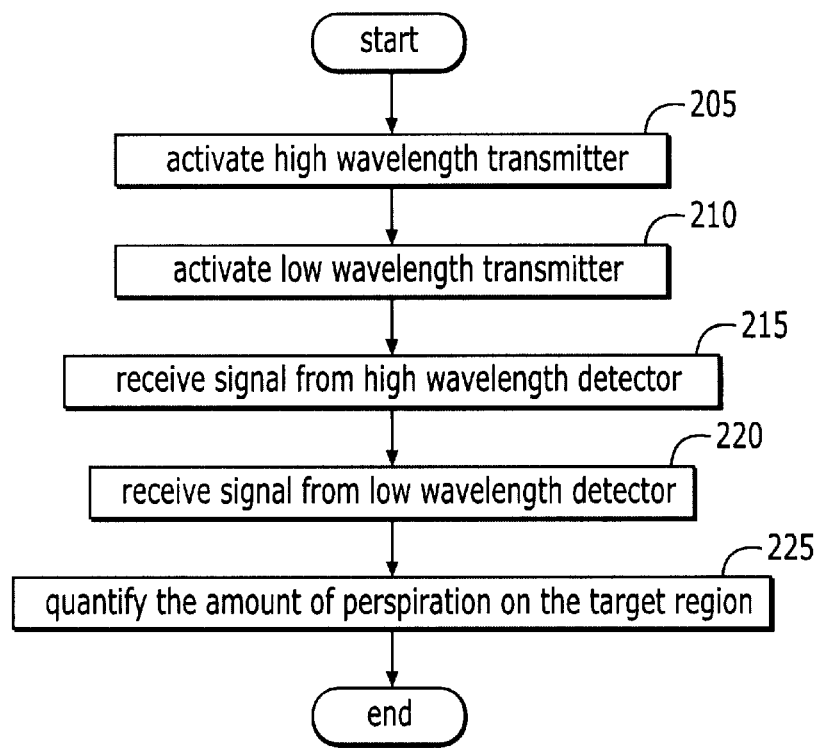
FIG. 3 presents a flow chart illustrating operations performed to quantify the dermal hydration of the target region, in accordance with the first embodiment.
Figure 4:
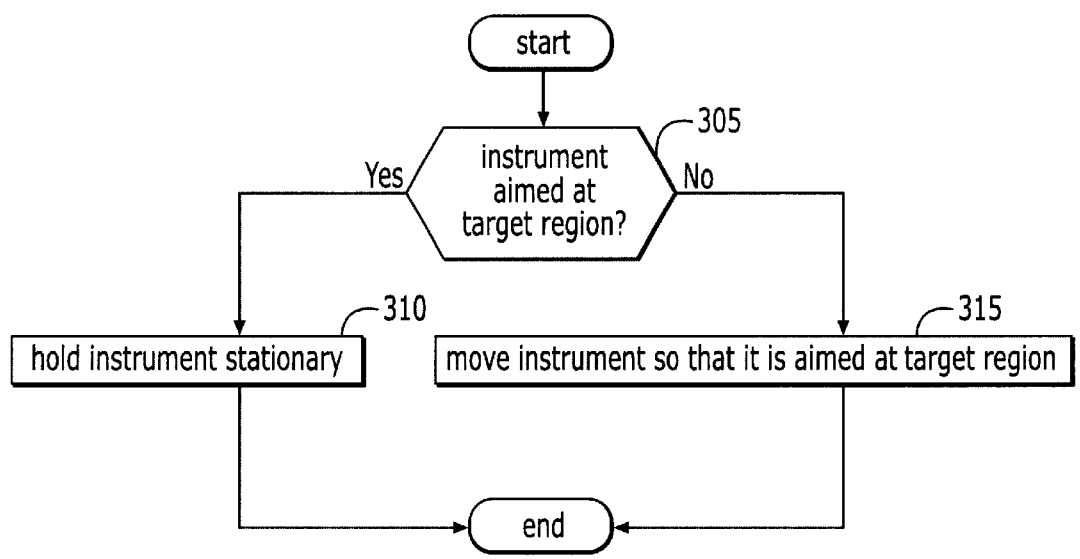
FIG. 4 presents a flow chart illustrating operations performed to track the target region, in accordance with the first embodiment.

The flow chart presented by FIG. 2 illustrates high level operations performed to generally remotely quantify dermal hydration at the target region 34 of the moving human subject 36, in accordance with the first embodiment. At step 105, the operations of tracking the target region 34 and quantifying the dermal hydration of the target region are contemporaneously performed. FIG. 3 presents a flow chart illustrating operations performed to quantify the dermal hydration of the target region 34 in the furtherance of step 105 of FIG. 2, in accordance with the first embodiment. FIG. 4 presents a flow chart illustrating operations performed to track the target region 34 in the furtherance of step 105 of FIG. 2, in accordance with the first embodiment.

Although the operations presented by the flowchart of FIG. 3 are illustrated as occurring sequentially, in accordance with the first embodiment those operations are preferably performed contemporaneously and continuously so long as control is at step 105 of FIG. 2. Referring to FIGS. 1 and 3, in accordance with the first embodiment, the operations illustrated by FIG. 3 are performed by the controller/processor 18. At step 205 the high wavelength transmitter 20 is activated so that it transmits the high wavelength signal 22. At step 210 the low wavelength transmitter 24 is activated so that it transmits the low wavelength signal 26. At step 215 a signal is received from the high wavelength detector 50 in response to the reflected beam portion 48 being incident upon the high wavelength detector. The signal received from the high wavelength detector 50 provides a measure of the intensity of the reflected beam portion 48 in the wavelength range to which the high wavelength detector is sensitive. At step 220 a signal is received from the low wavelength detector 52 in response to the passed beam portion 46 being incident upon the low wavelength detector. The signal received from the low wavelength detector 52 provides a measure of the intensity of the passed beam portion 46 in the wavelength range to which the low wavelength detector is sensitive.

At step 225 the amount of liquid, namely water and most preferably perspiration, in the target region 34 is quantified. In accordance with the first embodiment, the amount of liquid in the target region 34 is quantified by determining a relationship between the signal received from the high wavelength detector 50 at step 215 and the signal received from the low wavelength detector 52 at step 220. In accordance with the first embodiment, the relationship is a ratio. In accordance with a first specific example, the ratio of interest is the ratio of the signal received from the high wavelength detector 52 at step 215 to the signal received from the low wavelength detector at step 220. As indicated above, the high wavelength signal 22 is absorbed by liquid, namely water and most preferably perspiration, to a greater degree than the low wavelength signal 26. Accordingly, a decrease in the ratio of the signal from the high wavelength detector 50 to the signal from the low wavelength detector 52 is indicative of an increase in the amount of the liquid at the target region, and vice versa. In accordance with another specific example, the ratio of interest is the ratio of the signal received from the low wavelength detector 52 at step 220 to the signal received from the high wavelength detector 50 at step 215. Accordingly, an increase in the ratio of the signal from the low wavelength detector 52 to the signal from the high wavelength detector 50 is indicative of a decrease in the amount of liquid at the target region, and vice versa.

In accordance with one aspect of the first embodiment, in at least some conditions at least a general correlation can be made between the amount of liquid, namely water or perspiration, in the target region 34 and the stress level of the human subject 36. For example, increasing amounts of perspiration generally correspond to increased stress, and vice versa. More specifically, it is believed that the dermal hydration levels can be correlated with stress in a manner at least generally similar to that in which GSR data is correlated with stress. In accordance with an alternative embodiment, rather than relying upon the ratios as described above, more complex algorithms are provided for correlating the signals received from the high wavelength detector 50 at step 215 and the low wavelength detector 52 at step 220 to provide an indication of the amount of liquid, namely water and most preferably perspiration, at the target region 34.

Referring to FIGS. 1 and 4, at step 305 a determination is made as to whether the instrument 10 is aimed at the target region 34. In accordance with the first embodiment, this determination is made by the operator 58 looking through the telescopic sight 60 and determining if the intersection of the crosshairs within the telescopic sight are centered on the target region 34. As mentioned above and in accordance with the first embodiment, the transmitted beam 30 is incident upon the target region 34 and the field of view of the detecting mechanism 16 is upon the target region while the operator 58 is looking through the telescopic sight 60 and observes that the intersection of the crosshairs of the telescopic sight are centered on the target region. If it is determined at step 305 that the instrument 10 is aimed at the target region 34, as indicated by the crosshairs being centered on the target region as described above, control is transferred to step 310, where the instrument is held stationary by the operator 58. If it is determined at step 305 that the instrument 10 is not aimed at the target region, control is transferred to step 315, where the operator 58 moves the instrument so that it is aimed at the target region. The operations illustrated by FIG. 4 are repeated quickly and continuously in a loop-like fashion while control remains at step 105 of FIG. 2.

As described above, the present invention advantageously provides an indication of the amount of liquid, namely water and most preferably perspiration, at the target region 34 via a generally noninvasive examination that can be remotely conducted in a covert fashion. Some of these advantages are at least partially facilitated by the tracking operations described with reference to FIG. 4. Nonetheless, in accordance with an alternative embodiment of the present invention, the tracking operations are not utilized and other provisions are made for precluding relative movement between the instrument 10 and the subject 36 so that the instrument remains aimed at the target region 34 while quantifying the dermal hydration of the target region. Accordingly, the present invention preferably includes but does not necessarily require tracking.

A second embodiment of the present invention is identical to the first embodiment, except for variations noted and variations that will be apparent to those of ordinary skill in the art. Whereas in accordance with the first embodiment the tracking operations described with reference to FIG. 4 are performed manually by the operator 58, in accordance with the second embodiment the instrument 10 is equipped with an automated system for performing the tracking operations described with reference to FIG. 4. Such automated tracking systems are well known and commercially available, and accordingly the present invention is not limited to manual tracking.

In accordance with the first and second embodiments, the controller/processor 18 includes a computer program product. The computer program product includes a computer-readable storage medium having computer-readable program code devices, such as a series of computer instructions, embodied in the computer-readable storage medium for facilitating the operations of the present invention.

In this regard, FIGS. 2–4 are block diagram, flowchart and control flow illustrations of methods, systems and program products according to the invention. It will be understood that each block or step of the block diagram, flowchart and control flow illustrations, and combinations of blocks in the block diagram, flowchart and control flow illustrations, can be implemented by computer program instructions. These computer program instructions may be loaded onto a computer or other programmable apparatus to produce a machine, such that the instructions which execute on the computer or other programmable apparatus create devices for implementing the functions specified in the block diagram, flowchart or control flow block(s) or step(s). These computer program instructions may also be stored in a computer-readable memory that can direct a computer or other programmable apparatus to function in a particular manner, such that the instructions stored in the computer-readable memory produce an article of manufacture including instruction devices which implement the function specified in the block diagram, flowchart or control flow block(s) or step(s). The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the block diagram, flowchart or control flow block(s) or step(s).

Accordingly, blocks or steps of the block diagram, flowchart or control flow illustrations support combinations of devices for performing the specified functions, combinations of steps for performing the specified functions and program instruction devices for performing the specified functions. It will also be understood that each block or step of the block diagram, flowchart or control flow illustrations, and combinations of blocks or steps in the block diagram, flowchart or control flow illustrations, can be implemented by special purpose hardware-based computer systems which perform the specified functions or steps, or combinations of special purpose hardware and computer instructions.

As described above, the present invention advantageously provides an indication of the amount of liquid, namely water and most preferably perspiration, at the target region during noninvasive examinations that can be remote and covert. The amount of liquid at the target region can provide an indication of the level of stress of the subject being examined. It can be useful to examine subjects using the techniques of the present invention in a variety of situations. For example, the techniques of the present invention can be used in place of GSR testing, such as for examinations associated with security clearance and drug screening, and the like, to provide an indication as to whether an individual is being deceptive. Additionally, the present invention can be used to determine the physiological state of individuals that are at work or being trained, such as in the cockpit of an aircraft or in other locations where it can be beneficial to be aware of the stress, fatigue, anxiety or other physiological states of individuals. It can also be useful to utilize the present invention in combination with other examination techniques, such as, but not limited to, those described in U.S. Pat. No. 5,867,257 to Rice et al., and the like.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for quantifying dermal hydration, the method comprising:
   obtaining a first measurement of electromagnetic radiation that has been reflected from a region that is an exterior surface of skin and any liquid closely associated with the exterior surface of the skin;
   obtaining a second measurement of electromagnetic radiation that has been reflected from the region; and
   quantifying dermal hydration in the region by determining a relationship between the first and second measurements.

2. A method for quantifying dermal hydration, the method comprising:
   obtaining a first measurement of electromagnetic radiation that has been reflected from a region comprising skin and any liquid closely associated with the skin;
   obtaining a second measurement of electromagnetic radiation that has been reflected from the region;
   quantifying the amount of liquid in the region by determining a relationship between the first and second measurements; and
   tracking the region as the region moves, wherein the first and second measurements are obtained while tracking the region.

3. A method according to claim 1, wherein:
   the obtaining the first measurement comprises obtaining a measurement of a first type of electromagnetic radiation that has been reflected from the region; and
   the obtaining the second measurement comprises obtaining a measurement of a second type of electromagnetic radiation that has been reflected from the region and that is absorbed by a liquid to a greater degree than the first type of electromagnetic radiation is absorbed by the liquid.

4. A method according to claim 3, wherein the obtaining the first measurement and the obtaining the second measurement are contemporaneous.

5. A method according to claim 3, wherein:
   the obtaining the measurement of the first type of electromagnetic radiation comprises obtaining a measurement of electromagnetic radiation that is not detectable by a naked eye of a human; and
   the obtaining the measurement of the second type of electromagnetic radiation comprises obtaining a measurement of electromagnetic radiation that is not detectable by a naked eye of a human.

6. A method according to claim 5, wherein the obtaining the measurement of the second type of electromagnetic radiation comprises obtaining a measurement of electromagnetic radiation with at least one wavelength selected from the range of approximately 1500–1600 nm.

7. A method according to claim 6, wherein the obtaining the measurement of the first type of electromagnetic radiation comprises obtaining a measurement of electromagnetic radiation with at least one wavelength selected from the range of approximately 1000–1100 nm.

8. A method according to claim 3, further comprising transmitting the first and second types of electromagnetic radiation so that the first and second types of electromagnetic radiation are incident upon and reflected by the region.

9. A method according to claim 8, wherein the transmitting the first and second types of electromagnetic radiation comprises transmitting electromagnetic radiation that is not detectable by a naked eye of a human.

10. A method for quantifying dermal hydration at an exterior surface of skin, the method comprising:
    transmitting electromagnetic radiation so that the electromagnetic radiation is incident upon and reflected by the exterior surface of the skin and any liquid closely associated with the exterior surface of the skin, wherein the transmitting comprises transmitting a first type of electromagnetic radiation and transmitting a second type of electromagnetic radiation that is absorbed by liquid to a greater degree than the first type of electromagnetic radiation;
    detecting the reflected electromagnetic radiation; and
    quantifying dermal hydration, including taking into account the reflected electromagnetic radiation that has been detected.

11. A method for quantifying dermal hydration, the method comprising:
    transmitting electromagnetic radiation so that the electromagnetic radiation is incident upon and reflected by a region comprising skin and any liquid closely associated with the skin, wherein the transmitting comprises transmitting a first type of electromagnetic radiation and transmitting a second type of electromagnetic radiation that is absorbed by liquid to a greater degree than the first type of electromagnetic radiation;
    detecting the reflected electromagnetic radiation; and tracking the region as the region moves, wherein the transmitting and the detecting are carried out while tracking the region.

12. A method according to claim 10, wherein:
the transmitting the first type of electromagnetic radiation comprises transmitting electromagnetic radiation that is not detectable by a naked eye of a human; and
the transmitting the second type of electromagnetic radiation comprises transmitting electromagnetic radiation that is not detectable by a naked eye of a human.

13. A method according to claim 10, wherein the transmitting the second type of electromagnetic radiation comprises transmitting electromagnetic radiation with at least one wavelength selected from the range of approximately 1500–1600 nm.

14. A method according to claim 13, wherein the transmitting the first type of electromagnetic radiation comprises transmitting electromagnetic radiation with at least one wavelength selected from the range of approximately 1000–1100 nm.

15. An apparatus for quantifying dermal hydration at an exterior surface of skin, the apparatus comprising:
a transmitting mechanism for transmitting at least first and second types of electromagnetic radiation so that the first and second types of electromagnetic radiation are incident upon and reflected by the exterior surface of the skin and any liquid closely associated with the exterior surface of the skin, wherein the second type of electromagnetic radiation is absorbed by liquid to a greater degree than the first type of electromagnetic radiation; and
a detecting mechanism positioned for detecting the first and second types of electromagnetic radiation that are reflected by the exterior surface of the skin and any liquid closely associated with the exterior surface of the skin.

16. An apparatus according to claim 15, wherein the transmitting mechanism is operative so that the first and second types of electromagnetic radiation are not detectable by a naked eye of a human.

17. An apparatus according to claim 15, wherein:
the transmitting mechanism comprises:
a first transmitter for transmitting electromagnetic radiation with at least one wavelength selected from the range of approximately 1500–1600 nm, and
a second transmitter for transmitting electromagnetic radiation with at least one wavelength selected from outside of the range of the first transmitter; and
the detecting mechanism comprises:
a first detector for detecting electromagnetic radiation transmitted by the first transmitter, and
a second detector for detecting electromagnetic radiation transmitted by the second transmitter.

18. An apparatus for quantifying dermal hydration in a region, the apparatus comprising:
a transmitting mechanism for transmitting at least first and second types of electromagnetic radiation so that the first and second types of electromagnetic radiation are incident upon and reflected by the region, wherein the second type of electromagnetic radiation is absorbed by liquid to a greater degree than the first type of electromagnetic radiation; and
a detecting mechanism for detecting the first and second types of electromagnetic radiation that are reflected by the region,
wherein the detecting mechanism comprises a field of view, the transmitting mechanism transmits a beam that comprises the first and second types of electromagnetic radiation, and the apparatus further comprises a tracking mechanism for moving the field of view and the beam so that the region remains in the field of view and in the beam as the region moves.

19. An apparatus according to claim 15, further comprising a housing that contains both the detecting mechanism and the transmitting mechanism.

20. An apparatus according to claim 19, wherein:
the transmitting mechanism comprises:
a first transmitter for transmitting the first type of electromagnetic radiation,
a second transmitter for transmitting the second type of electromagnetic radiation, and
a beam combiner positioned so that both the first type of electromagnetic radiation transmitted by the first transmitter and the second type of electromagnetic radiation transmitted by the second transmitter are incident upon the beam combiner and the first and second types of electromagnetic radiation are together transmitted from the beam combiner in a beam that is incident upon the region so that at least a portion of the beam is reflected by the region; and
the detecting mechanism comprises:
a beam splitter positioned so at least a portion of the beam that is reflected by the region is incident upon the beam splitter and split into first and second portions,
a first detector for detecting the first type of electromagnetic radiation and positioned so that the first portion is incident upon the first detector, and
a second detector for detecting the second type of electromagnetic radiation and positioned so that the second portion is incident upon the second detector.

21. An apparatus according to claim 20, further comprising:
structure defining a first aperture positioned so that the beam transmitted from the beam combiner passes through the first aperture prior to being incident upon the region; and
structure defining a second aperture positioned so that at least the portion of the beam that is reflected by the region passes through the second aperture prior to being incident upon the beam splitter.

22. An apparatus for quantifying dermal hydration in a dermal region, the apparatus comprising:
a detecting mechanism positioned for obtaining at least first and second measurements of electromagnetic radiation that has been reflected from the dermal region, wherein the dermal region is an exterior surface of skin and any liquid closely associated with the exterior surface of the skin, so that the detecting mechanism is positioned for obtaining the first and second measurements of electromagnetic radiation that has been reflected from the exterior surface of the skin and any liquid closely associated with the exterior surface of the skin; and
a processor operationally associated with the detecting mechanism for quantifying the amount of liquid in the region by determining a relationship between the first and second measurements.

23. An apparatus for quantifying dermal hydration in a region, the apparatus comprising:
a detecting mechanism for obtaining at least first and second measurements of electromagnetic radiation that has been reflected from the region; and a processor operationally associated with the detecting mechanism for quantifying the amount of liquid in the region by determining a relationship between the first and second measurements, wherein the detecting mechanism comprises a field of view and the apparatus further comprises a tracking mechanism for moving the field of view so that the field of view tracks movements of the region.

24. An apparatus according to claim 23, further comprising a transmitting mechanism operative for transmitting electromagnetic radiation so that transmitted electromagnetic radiation is incident upon the region and reflected by the region to the detecting mechanism, wherein the transmitting mechanism is operative for transmitting a beam that comprises electromagnetic radiation that is at least partially absorbed by liquid, and the tracking mechanism is further operative for moving the beam so that the beam tracks movements of the region.

25. An apparatus according to claim 22, wherein the detecting mechanism is operative so that:

the first measurement is a measurement of a first type of electromagnetic radiation that has been reflected from the region; and the second measurement is a measurement of a second type of electromagnetic radiation that has been reflected from the region and that is absorbed by a liquid to a greater degree than the first type of electromagnetic radiation is absorbed by the liquid.

26. An apparatus according to claim 25, wherein the detecting mechanism comprises:

a first detector for detecting electromagnetic radiation with at least one wavelength selected from the range of approximately 1500–1600 nm; and a second detector for detecting electromagnetic radiation with at least one wavelength selected from outside the range of the first detector.

27. An apparatus according to claim 22, further comprising a transmitting mechanism operative for transmitting electromagnetic radiation so that transmitted electromagnetic radiation is incident upon the region and reflected by the region to the detecting mechanism.

28. An apparatus according to claim 27, further comprising a housing that contains both the detecting mechanism and the transmitting mechanism.

29. An apparatus according to claim 27, wherein the detecting mechanism is operative so that:

the first measurement is a measurement of a first type of electromagnetic radiation that has been reflected from the region; and the second measurement is a measurement of a second type of electromagnetic radiation that has been reflected from the region and that is absorbed by a liquid to a greater degree than the first type of electromagnetic radiation is absorbed by the liquid.

30. An apparatus according to claim 29, wherein the detecting mechanism comprises:

a first detector for detecting electromagnetic radiation with at least one wavelength selected from the range of approximately 1500–1600 nm; and a second detector for detecting electromagnetic radiation with at least one wavelength selected from outside the range of the first detector.

* * * * *